United States Patent
Tan et al.

(10) Patent No.: US 9,839,368 B2
(45) Date of Patent: Dec. 12, 2017

(54) SYSTEMS AND METHODS FOR FILTERING ECG ARTIFACTS

(71) Applicant: ZOLL MEDICAL CORPORATION, Chelmsford, MA (US)

(72) Inventors: Qing Tan, Winchester, MA (US); Frederick J. Geheb, Danvers, MA (US); Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 69 days.

(21) Appl. No.: 13/743,891

(22) Filed: Jan. 17, 2013

(65) Prior Publication Data

US 2013/0184600 A1    Jul. 18, 2013

Related U.S. Application Data (60) Provisional application No. 61/587,433, filed on Jan. 17, 2012.

(51) Int. Cl.
*A61B 5/04* (2006.01)
*A61B 5/00* (2006.01)
(Continued)

(52) U.S. Cl.
CPC ........ *A61B 5/04017* (2013.01); *A61B 5/0531* (2013.01); *A61B 5/4836* (2013.01);
(Continued)

(58) Field of Classification Search
CPC .... A61N 1/39; A61B 5/04017; A61B 5/0402; A61B 5/11; A61B 5/721; A61B 5/4836; A61B 5/7217
(Continued)

(56) References Cited

U.S. PATENT DOCUMENTS

| 4,683,890 A | 8/1987 | Hewson |
| 6,351,671 B1 | 2/2002 | Myklebust et al. |

(Continued)

FOREIGN PATENT DOCUMENTS

| DE | 3110915 A1 | 12/1982 |
| WO | 2006006871 A2 | 1/2006 |

OTHER PUBLICATIONS

Aramendi et al. "A Simple Effective Filtering Method for Removing CPR Caused Artefacts from Surface ECG Signals". Computers in Cardiology. Sep. 25, 2005.

(Continued)

*Primary Examiner* — Lindsey G Wehrheim
(74) *Attorney, Agent, or Firm* — Fish & Richardson P.C.

(57) ABSTRACT

Systems and methods of processing raw electrocardiogram (ECG) waveform data of a patient into estimated real-time ECG waveform data. The method includes sensing-at least one physical non-cardiac influence on the raw ECG waveform data, constructing a time domain computer model of the at least one physical, non-cardiac influence on the raw ECG waveform data, and adaptively filtering the raw ECG waveform data in the time domain using the constructed time domain computer model of the at least one physical non-cardiac influence on the raw ECG waveform data to form the estimated real-time ECG waveform data. The system can include an ECG device for collecting raw ECG waveform data, at least two ECG electrodes positioned on the patient and electrically coupled to the ECG device, and a processor coupled to the ECG device and configured to compute a time domain model of an artifact created by chest compressions.

18 Claims, 3 Drawing Sheets

(51) Int. Cl.
  *A61B 5/053* (2006.01)
  *A61B 5/11* (2006.01)
  *A61B 5/0402* (2006.01)
  *A61N 1/39* (2006.01)
  *A61H 31/00* (2006.01)

(52) U.S. Cl.
  CPC ............ *A61B 5/721* (2013.01); *A61B 5/7217* (2013.01); *A61N 1/3925* (2013.01); *A61B 5/0402* (2013.01); *A61B 5/11* (2013.01); *A61H 31/004* (2013.01); *A61H 2201/501* (2013.01); *A61H 2201/5007* (2013.01); *A61H 2201/5061* (2013.01); *A61H 2201/5071* (2013.01); *A61H 2201/5079* (2013.01); *A61H 2201/5084* (2013.01); *A61H 2201/5097* (2013.01); *A61H 2230/10* (2013.01); *A61N 1/39* (2013.01)

(58) Field of Classification Search
  USPC .................. 600/481, 508, 509, 513; 327/556
  See application file for complete search history.

(56) References Cited

U.S. PATENT DOCUMENTS

| | | |
|---|---|---|
| 6,356,785 B1 | 3/2002 | Snyder et al. |
| 6,749,567 B2 | 6/2004 | Davis et al. |
| 7,308,304 B2 | 12/2007 | Hampton et al. |
| 2001/0047140 A1 | 11/2001 | Freeman |
| 2004/0082888 A1* | 4/2004 | Palazzolo .......... A61B 5/04012 601/41 |
| 2004/0143298 A1 | 7/2004 | Nova et al. |
| 2004/0210170 A1 | 10/2004 | Palazzolo et al. |
| 2006/0015044 A1 | 1/2006 | Stavland et al. |
| 2007/0010764 A1 | 1/2007 | Palazzolo et al. |
| 2007/0135739 A1 | 6/2007 | Halperin et al. |
| 2007/0197926 A1 | 8/2007 | Danehorn et al. |
| 2007/0299473 A1 | 12/2007 | Matos |
| 2008/0208082 A1 | 8/2008 | Nysaether et al. |
| 2009/0036794 A1* | 2/2009 | Stubhaug .............. A61B 5/053 600/547 |
| 2010/0164612 A1* | 7/2010 | Koyrakh ...................... 327/556 |
| 2010/0292748 A9 | 11/2010 | Stickney et al. |
| 2010/0317981 A1* | 12/2010 | Grunwald ..................... 600/509 |
| 2011/0034836 A1* | 2/2011 | Halperin et al. ................ 601/41 |
| 2011/0066054 A1* | 3/2011 | Yazicioglu et al. .......... 600/509 |
| 2011/0105930 A1* | 5/2011 | Thiagarajan ....... A61B 5/04017 600/523 |
| 2012/0150169 A1 | 6/2012 | Zielinksi et al. |
| 2012/0191024 A1 | 7/2012 | Halperin et al. |
| 2014/0093853 A1 | 4/2014 | Constantine, III |

OTHER PUBLICATIONS

International Search Report and Written Opinion for PCT/US2013/21934 dated Apr. 1, 2013.

Romero et al. "Motion Artifact Reduction in Ambulatory ECG Monitoring: An Integrated System Approach". Wireless Health. Oct. 10, 2011.

* cited by examiner

SYSTEMS AND METHODS FOR FILTERING ECG ARTIFACTS

CROSS REFERENCE TO RELATED APPLICATIONS

This application claims priority under 35 U.S.C. §119(e) to U.S. Provisional Application Ser. No. 61/587,433 titled "SYSTEMS AND METHODS FOR FILTERING ECG ARTIFACTS," filed Jan. 17, 2012, which is incorporated herein by reference in its entirety.

BACKGROUND

According to American Heart Association guidelines, resuscitation treatments for patients suffering from cardiac arrest generally include applying chest compressions to provide blood flow to the victim's heart, brain and other vital organs, clearing and opening the patient's airway, and providing rescue breathing for the patient. The term cardiopulmonary resuscitation (CPR) refers to an emergency procedure that includes chest compressions and which may additionally include breathing. Resuscitation treatments may include establishing a permanent airway through intubation, with subsequent periodic provision of air to the lungs via positive pressure support. If the patient has a shockable heart rhythm, as determined by electrocardiogram (ECG) data, resuscitation may also include defibrillation therapy.

ECG data is generated using multiple electrode pads placed at various positions on the patient's body. Electrode pads are often placed on a patient's chest. CPR compressions may cause artifacts to appear on ECG recordings, making them difficult or impossible to interpret. Thus, rescue workers often stop CPR compressions to obtain accurate ECG recordings and determine whether defibrillation therapy should be applied or whether a prior defibrillation attempt was successful. However, studies have shown that stopping CPR compressions may have a detrimental effect on patient survival. Current American Heart Association (AHA) protocols for cardiac life support emphasize the importance of uninterrupted chest compressions. Therefore, interruptions to assess heart rhythm should be minimized.

SUMMARY

In accordance with one aspect of the present invention, a method of processing raw electrocardiogram (ECG) waveform data of a patient into estimated real-time ECG waveform data is provided. The method comprises sensing at least one physical non-cardiac influence on the raw ECG waveform data, constructing a time domain computer model of the at least one physical, non-cardiac influence on the raw ECG waveform data, and adaptively filtering the raw ECG waveform data in the time domain using the constructed time domain computer model of the at least one physical non-cardiac influence on the raw ECG waveform data to form the estimated real-time ECG waveform data In accordance with one embodiment, the at least one physical non-cardiac influence on the raw ECG waveform is caused by repeated chest compressions, and constructing a time domain computer model includes collecting several cycles of chest compressions and calculating a chest compression artifact.

In accordance with another embodiment, adaptively filtering the raw ECG waveform data includes subtracting the constructed time domain computer model of the at least one physical non-cardiac influence from the raw ECG waveform data.

In accordance with each of the above embodiments, the method may further comprise detecting a frequency of repetition of the at least one physical non-cardiac influence on the raw ECG waveform.

In accordance with another embodiment, sensing at least one physical non-cardiac influence on the raw ECG waveform includes sensing the at least one physical non-cardiac influence on the raw ECG waveform at one of an ECG electrode, a pad placed beneath the patient, the patient's skin, an ECG monitoring device, a manually operated chest compression device, and an automatic electro-mechanical chest compression device.

In accordance with another embodiment, sensing at least one physical non-cardiac influence on the raw ECG waveform includes detecting the at least one physical non-cardiac influence on the raw ECG waveform data in the ECG waveform data.

In accordance with some embodiments, sensing at least one physical non-cardiac influence on the raw ECG waveform includes receiving data from a chest compression device including at least one of chest compression rate and chest compression force.

In accordance with any of the above-described embodiments, sensing at least one physical non-cardiac influence on the raw ECG waveform includes measuring a change in impedance of an interface between an ECG electrode and the patient during chest compressions, and constructing the time domain computer model includes determining an effect of the change in impedance on the raw ECG waveform data. In accordance with one aspect of this embodiment, measuring the change in impedance includes measuring a change in complex impedances of the interface between the ECG electrode and the patient during the chest compressions over a range of frequencies lying between 30 kHz and 100 kHz. In accordance with another aspect of this embodiment, measuring the change in impedance includes measuring a change in complex impedances of the interface between the ECG electrode and the patient during the chest compressions over a range of frequencies lying between 30 kHz and 70 kHz. In accordance with a further aspect of this embodiment, measuring the change in impedance includes measuring a change in complex impedances of the interface between the ECG electrode and the patient during the chest compressions at a frequency of about 35 kHz. In accordance with another aspect of this embodiment, measuring the change in impedance includes applying plural superposed waveforms in a quadrature relationship to each other to the electrode and computing a complex impedance from detected phase, amplitude, and frequency information.

In accordance with another aspect of the present invention, a medical device system is provided. The medical device system, comprises a electrocardiogram (ECG) device for collecting raw ECG waveform data from a patient, at least two ECG electrodes positioned on the patient and electrically coupled to the ECG device, and a processor coupled to the ECG device and configured to compute a time domain model of an artifact created by chest compressions.

In accordance with one embodiment, the medical device system further comprises at least one first sensor for detecting the chest compressions applied to the patient. In accordance with some embodiments, the medical device system can further comprise a second sensor, where the first sensor and the second sensor are configured to calculate impedance of an interface between at least one of the at least two ECG electrodes and the patient. In accordance with each of these embodiments, the at least one first sensor is located at one ECG electrode of the at least two ECG electrodes, a pad placed beneath the patient, the patient's skin, a manually operated chest compression device, and an automatic electro-mechanical chest compression device.

In accordance with one or more embodiments, the processor is further configured to detect the artifact based on the raw ECG waveform data. In accordance with various embodiments, the medical device system can further comprise an automatic electro-mechanical chest compression device configured to apply chest compressions to a patient and to provide chest compression data to the processor.

In accordance with each of the above described embodiments, the medical device system can further comprise at least one continuous notch filter configured to filter the raw ECG waveform and provide a filtered ECG waveform to the processor, the at least one continuous notch filter including at least one first continuous notch filter having a center frequency corresponding to a frequency of the chest compressions. In accordance with a further embodiment, the at least one continuous notch filter further includes at least one second continuous notch filter having a center frequency corresponding to a first harmonic of the frequency of the chest compressions.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Devices may be used to detect and analyze electrocardiography (ECG) signals acquired from a patient to determine when a cardiac arrhythmia exists and, if an arrhythmia does exist, whether it is treatable by defibrillation therapy. However, noise caused by external factors may induce artifacts in the ECG data. For example, applying chest compressions to the patient induces artifacts in the ECG signal. To observe a clean and substantially error-free ECG signal and determine whether defibrillation therapy would be beneficial, a rescue worker temporarily discontinues chest compressions. However, many studies have reported that the discontinuation of chest compressions, such as is commonly done for ECG analysis, can significantly reduce the recovery rate of spontaneous circulation and 24-hour survival rate. Therefore, there is a need to assess cardiac rhythm during continuous chest compressions.

One aspect of the present invention is directed to techniques for filtering out artifacts caused by chest compressions from an ECG signal, thereby allowing chest compressions to continue while also observing a substantially error-free ECG signal. In one embodiment, one or more filters identify and filter out chest compression artifacts. When chest compression artifacts are identified, a filtering algorithm is used to identify and/or remove or substantially remove noise induced by the chest compressions from the ECG signal. The filtering algorithm may be a time domain filter. Additionally, the filtering algorithm may be adaptive such that it identifies the different artifacts created by different rescue workers applying chest compressions, or different artifacts resulting from rescue worker fatigue, and adjusts the filter accordingly.

In one embodiment, adaptive algorithms may be used to generate a time domain model of the compression noise. The model may be used to optimize the ECG waveform during CPR. For example, an inverse noise signal may be generated using the time domain model of the compression noise and the inverse noise signal may be subtracted from a raw ECG signal at a point in time and/or space prior to the point in the raw ECG signal where the compression noise will influence the ECG. In one example, the inverse noise signal is generated using previously recorded raw ECG signal data. The previously recorded raw ECG signal may be the previous few seconds of raw ECG signal recorded from the patient.

A significant source of CPR compression-caused artifacts in an ECG signal may be due to a charge transfer effect in the electrolyte gel used when attaching the electrode pads to the patient's skin. The magnitude of the charge transfer effect may depend on how much of each electrode pad lies under a compression pad or, in the case of manual compressions, how much of each electrode pad lies under the compression surface. One source of ECG artifacts is the charge transfer effect of the electrode pads on ECG measurements. Complex impedance measurements may be used to measure, characterize and remove the ECG artifact created by the interface between the skin and one or more ECG electrode pads. In particular, ECG artifacts arise from skin changes due to skin hydration from the electrolyte gel at the location of the electrode pads. As the skin hydrates, electrode pad performance changes. For example, the ECG artifact may decrease over time as the skin hydrates, and the filter removing the artifact may use complex impedance measurements to identify and adjust to the decreasing amplitude of the artifact caused by the skin hydrating.

According to one embodiment, complex impedance measurements can include measuring the change of impedance by applying plural superposed waveforms in a quadrature relationship to each other and to the electrode pads, and computing the complex impedance from detected phase, amplitude, and frequency information. According to one example, complex impedance is measured over a range of frequencies between about 30 kHz and about 100 kHz. According to another example, complex impedance is measured over a range of frequencies between about 30 kHz and about 70 kHz. According to further examples, complex impedance is measured over at a frequency of about 30 kHz, about 35 kHz, 40 kHz, 45 kHz, or 50 kHz.

Figure 1:
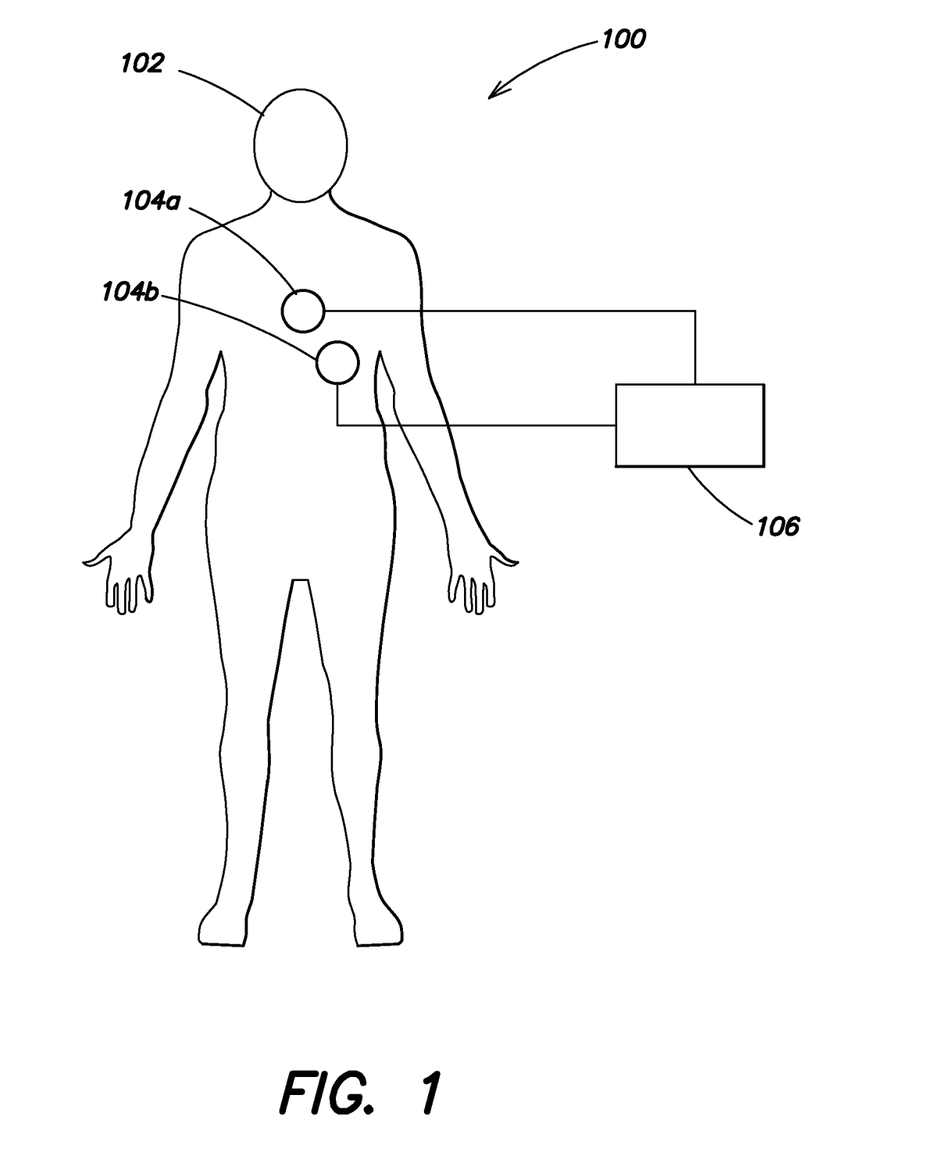
FIG. 1 is a schematic diagram of a patient with electrocardiography electrode pads, in accordance with one embodiment.

FIG. 1 is a schematic diagram 100 of a patient 102 with ECG electrode pads 104a-104b, and an ECG device 106. The ECG device 106 collects ECG data from the patient using the electrode pads 104a and 104b. The ECG device 106 may be an Automated External Defibrillator (AED) device, which determines, based on the ECG data, whether the patient 102 would benefit from defibrillation therapy, and if so, can apply a defibrillating shock to the patient. During emergency life support procedures, ECG measurements are usually made using two electrode pads 104a and 104b secured to the patient's chest. However, more than two electrode pads 104a and 104b may be used, placed at various positions on the patient's body.

When a patient receives CPR, in some instances an automatic electro-mechanical chest compression device is secured to the patient 102 to deliver the chest compressions to the patient 102. In one example, the automatic electro-mechanical chest compression device is a Zoll AutoPulse® cardiac support pump, which includes a board on which the patient is placed and a load-distributing band attached to the board that squeezes the patient's entire chest to deliver the compressions. In other instances, when a patient receives CPR, the patient receives manual compressions from a rescue worker. The rescue worker may use a small device while performing chest compressions to measure one or more of the compression rate, compression depth, and the compression pressure. In one example, the device is a Zoll PocketCPR® unit that the rescue worker places on the patient's chest while performing chest compressions.

Figure 2:
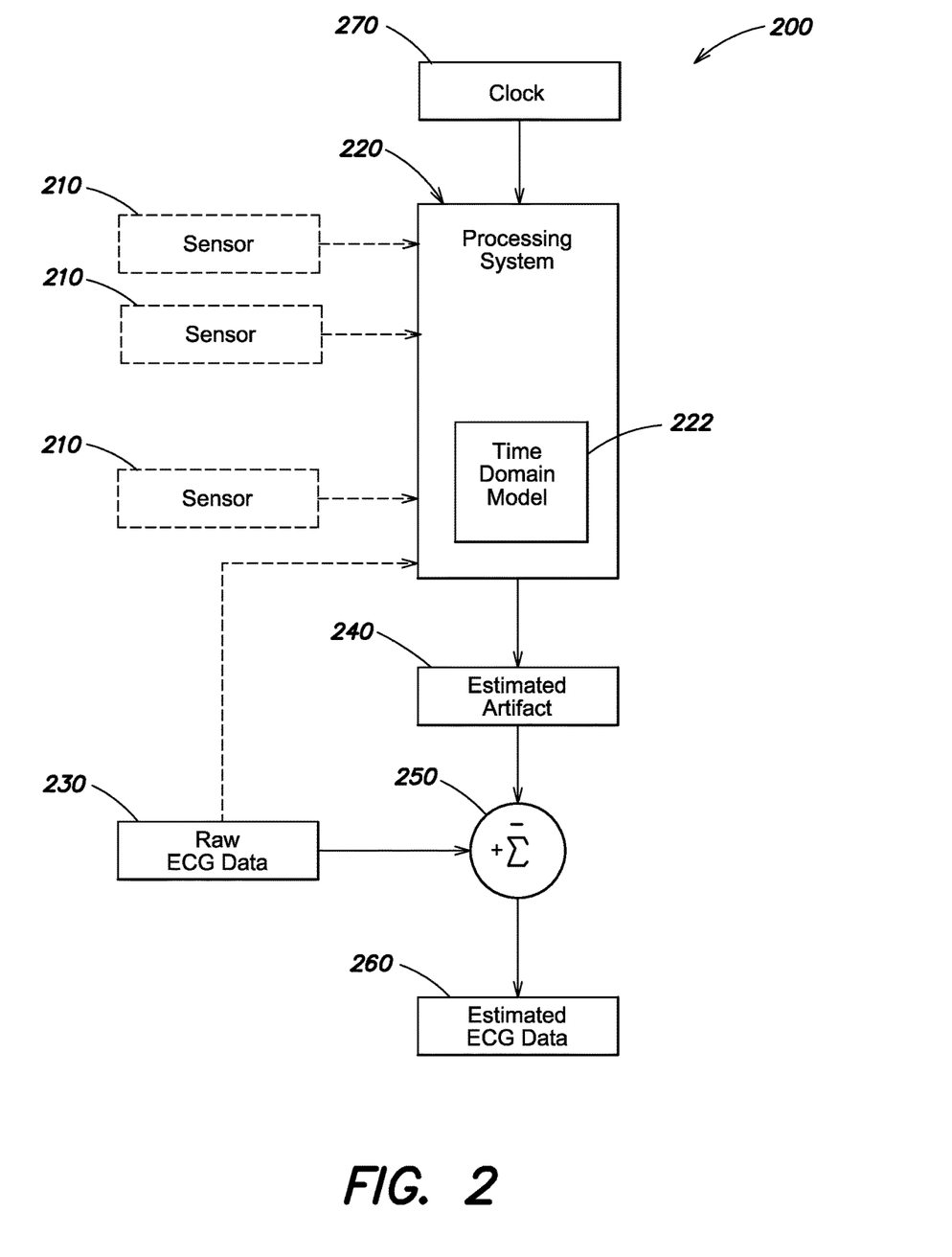
FIG. 2 is a data flow diagram for processing sensor data and electrocardiography data, in accordance with one embodiment.
Figure 3:
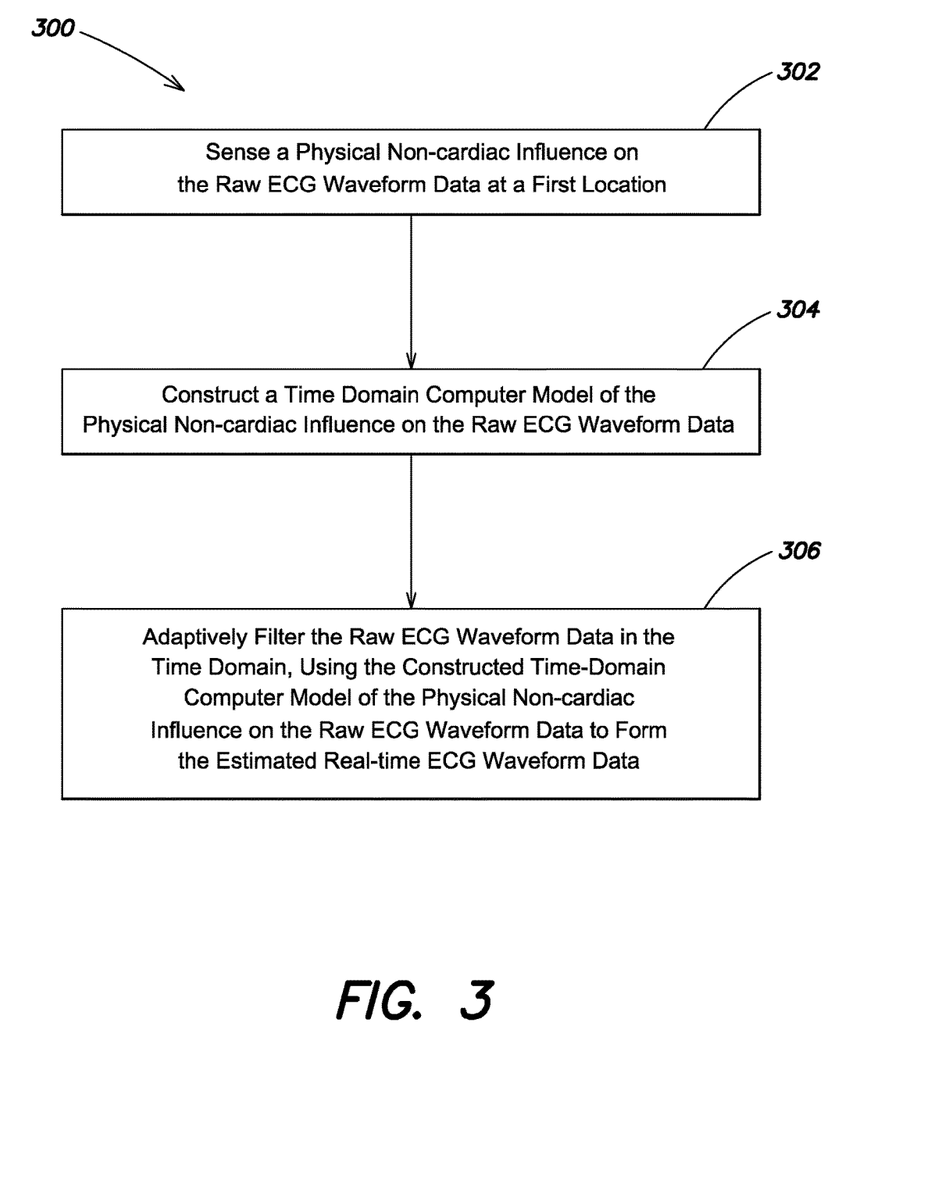
FIG. 3 is a flow chart of a method for processing ECG data, in accordance with another embodiment.

Whether chest compressions are delivered automatically by an electro-mechanical companion device or manually, one or both of the electrode pads 104a-104b are generally positioned at least partially underneath the automatic electro-mechanical chest compression device or beneath the hands of the rescue worker providing the chest compressions. The pressure of the chest compressions on the electrode pads 104a and 104b results in artifacts in the ECG data. A filtering algorithm, described in greater detail with respect to FIGS. 2 and 3, is used to remove or substantially remove the chest compression artifacts from the ECG data.

In one embodiment, one or more sensors are used to detect the chest compressions. The sensors may be pressure sensors, impedance sensors, accelerometers, motion sensors, or any other type of sensor. In various examples, the sensors measure chest compression acceleration, chest compression velocity, chest compression displacement, chest impedance and chest compression rate. Acceleration, velocity, displacement and compression rate may be measured using one or more sensors. Impedance may be measured between two or more sensors. According to various examples, the sensors may be located on a pad placed beneath the patient 102, on the patient 102, on the automatic electro-mechanical chest compression device, on the hand or arms of a rescue worker, or they may be secured to the patient's skin. An automatic electro-mechanical chest compression device may include sensors. For example, the Zoll AutoPulse® cardiac support pump includes load cell sensors on the board positioned beneath the patient 102. In other examples, one or more sensors may be attached to the electrode pads 104a and 104b.

Data detected by the sensors may be used to generate a model of the chest compression noise that manifests as artifacts in the ECG data, according to an embodiment of the invention. The model of the chest compression noise may be used to predict or estimate ECG artifacts, which may be filtered out from ECG data. In one example, the filtering algorithm uses a time domain model to remove the compression artifacts, and the predicted or estimated ECG artifacts are subtracted in the time domain from the raw ECG data to reduce or substantially eliminate the artifacts from the resulting ECG signal. According to various examples, as discussed above, artifacts may be caused by variations in electrode pad behavior and electrode pad response due to compression of the electrode pad-skin interface or skin stretching under the electrode pads. In another example, the artifact may be caused by compression effects on the patient's underlying tissues and organs.

The filtering algorithm may be used predictively to filter artifacts from future ECG data, and it may be adapted just before each compression to account for the most recent artifact data. The filtering algorithm may be adapted prior to each compression based upon data from the most recent two or more compression cycles. Averaging the ECG data over a few compression cycles accentuates the artifacts, which may then be filtered from past or future ECG data. In one example, the artifact data from a few compression cycles is used predictively to filter the next compression cycle. Previously calculated artifact data may be subtracted from the ECG data as it is recorded. In another example, the filtering algorithm includes ECG data from the current compression cycle, delaying the filtered ECG output signal. The average of the previous few cycles may be repeatedly calculated and the predicted artifact repeatedly updated for filtering upcoming cycles of ECG data. In various examples, the filtering algorithm may be adapted based upon data from the most recent three, four, five, six, eight, ten, twelve, fifteen, twenty, or all of the previous compression cycles. According to one embodiment, the filtering algorithm is a time domain filter, created by averaging the ECG over a few cycles of artifacts. A time domain filter may be especially effective at removing artifacts from rhythmic or cyclical ECG data.

When compressions are provided by an automatic electro-mechanical chest compression device, the compressions, and the resulting compression artifacts, are typically consistent. When the compression artifacts are similar or consistent, combining artifacts over multiple cycles results in a fairly accurate estimated artifact. The artifact waveform for chest compressions provided by an automatic electro-mechanical compression device resembles an AC-coupled, low-pass filtered square wave. Because of the high leading edge of the waveform and the quick falling edge, the load cell signals of electro-mechanical CPR devices can be filtered using the frequency response of the ECG to produce an artifact-predictive signal. The consistent artifact created by electro-mechanical compressions may be measured and used to produce an artifact-predictive signal that may be fed forward and subtracted form the ECG data in real time. According to another embodiment, the mechanical CPR device may provide information on the compression phase or pressure directly to the ECG device or the device processing the raw ECG input data and sensor data is not used.

When compressions are provided manually by a rescue worker, the compressions may be more variable over time, for example due to rescue worker fatigue. Thus, the filter may use fewer cycles of compressions to estimate the compression artifact created by manual compressions than it uses to estimate the compression artifact created by automatic electro-mechanical compressions. Furthermore, rescue workers usually take turns providing manual compressions. Since each rescue worker may provide compressions at a different rate and/or with a different amount of pressure or force, the filter is reset each time a different rescue worker begins providing the compressions. According to one embodiment, for manual compressions, an accelerometer or other sensor may be used to generate phase data and an artifact-predictive signal to be fed forward and subtracted from the ECG in real time.

In various examples, the filter may be a time domain filter, a Kalman filter, an autoregressive moving average (ARMA) filter, an adaptive notch filter, or a template-based filter. In one example, a Kalman filter may be used to predict the artifact to be subtracted from the ECG data in a continuously adaptive process. According to one embodiment, a heterodyne process is used to filter out the compression artifact by filtering the compression artifact in time with a carrier signal. The carrier signal is created by a local oscillator and set to be close in frequency to the frequency of the compression rate. The heterodyne process may be used to modulate the amplitude of the artifact.

According to one example, a phase-lock loop system is used to demodulate the compression artifact and remove it. In particular, the phase-locked loop control system may be used to track the frequency of the compression artifact and generate an output signal to demodulate it. According to one example, the phase-lock loop system is a circuit that includes a variable frequency oscillator and a phase detector. According to one aspect, the circuit compares the phase of the input compression signal with the phase of the signal from its output oscillator and adjusts the frequency of its oscillator to keep the phases matched. A feedback loop is used to control the oscillator frequency based on the signal detected by the phase detector.

According to one example, as described above, impedance measurements from two or more sensors secured to the patient's skin may be used to measure, characterize and remove the effect of the skin-electrode pad 104a-104b interface on ECG measurements. In one example, one or more of the impedance-measuring sensors are attached to one of the electrode pads 104a, and one or more of the impedance-measuring sensors are attached to the other electrode pad 104b.

According to one aspect, the sensors may be configured to send data to a central unit. The sensors may send the data through a cable or wirelessly. The central unit may be a computer or a computer processor connected to the ECG device, which applies one or more filtering algorithms and provides estimated real-time ECG data. In another example, the central unit or another device may be configured to send the sensor data and/or ECG data to a remote system, such as a monitoring station at a hospital, so that a medical professional who is not with the patient can monitor the patient's vital signs and/or ECG.

In one embodiment, the sensors may be attached to or integrated with a medical device, such as a cardiac support pump, CPR assist device or chest compression device. These sensors may be configured to detect artifacts caused by the medical device or by a rescuer who is applying chest compressions manually.

In one embodiment, the sensors are coupled to one or more transmitters configured to transmit data generated by the sensors to a central processing device, such an automatic emergency defibrillator (AED) or other device that analyzes ECG waveforms. The central processing device may be a device travelling with the patient or a remote device, such as a monitoring station at a hospital or doctor's office. The transmitters may be wireless transmitters, or the transmitters may transmit data through a cable or other wired-based interfaces. Various conventional wireless technologies may be used, including wireless USB, WiFi™, Bluetooth®, and Zigbee®. Other, more long range, technologies may also be used, such as CDMA, GSM, 3G or 4G. The protocol used to transmit the data may be configured to preserve phase (time) information associated with the noise being measured so as to enable the various signals to be time-correlated.

FIG. 2 shows a data flow diagram 200 for processing ECG data, and, optionally, sensor data, according to one embodiment. The processing system 220 is configured to compute a time-domain model 222 of an influence of the sensor data on raw ECG waveform data 230. In some embodiments, the processing system 220 detects artifacts in the ECG signal without using sensor data. For example, using a time domain filter model, the processing system 220 may identify cyclically repeated noise, from which it can determine the compression rate and aggregate two or more cycles of artifacts to amplify the artifact noise and filter it from the ECG signal. In another example, the processing system 220 may receive data directly from an automatic electro-mechanical chest compression device indicating the rate and force at which it is applying chest compressions.

Sensor data 210 from one or more sensors may be received by the processing system 220, such as a system having a general purpose or special purpose processor. In the case where sensor data 210 is received from more than one sensor, the processing system 220 is configured to compute the time domain model 222 of the data of one sensor relative to data from one or more other sensors. In one example, if each sensor is sensing at a different location, then the time-domain model 222 will reflect the combined or cumulative effects of the data sensed at each different location. For example, noise induced into an ECG signal of the patient 102 may result from compressions, and depending on the type of sensor (e.g., a pressure sensor, accelerometer, impedance sensor) and depending on oscillation phases, the sensor data may have an additive or subtractive effect on other sensor data and on the ECG at any given point in time. In another example, two or more phases of a signal from a particular sensor may be added together. Accordingly, the time domain model 222 may be adapted to account for compression effects by comparing the sensor data 210 from each sensor to identify noise components emanating from each sensor.

In one embodiment, the time domain model 222 is used to estimate at least one artifact 240 that results from the influence of compressions on the raw ECG data 230. Sensor data 210 may provide a fiducial point relating to each compression, allowing the time domain model 222 to align the cycles and add the ECG data, thereby accentuating the compression artifact. The estimated artifact 240 may be added to, subtracted from, or combined with the raw ECG data 230 using an adder 250 or other appropriate technique to provide estimated ECG data 260. The estimated ECG data 260 represents the raw ECG data 230 without or substantially without the artifacts.

In some embodiments, the processing system 220 detects artifacts in the ECG signal without using sensor data. For example, the processing system 220 may be able to determine the frequency of compression cycles from prominent ECG artifacts, and use a time domain model 222 to align two or more compression cycles to accentuate the compression artifact. As described above, the estimated artifact 240 may be added to, subtracted from, or otherwise combined with the raw ECG data 230 using an adder 250 or other appropriate technique to provide estimated ECG data 260.

According to another embodiment, the time-domain model 222 is used to estimate at least one artifact created by the skin-to-electrode interface described above. The artifact created by the skin-to-electrode interface may be determined using complex impedance measurements from two or more sensors positioned on the patient's skin. The estimated artifact 240 may be added to, subtracted from, or combined with the raw ECG data 230 using an adder 250 or other appropriate technique to provide estimated ECG data 260. The estimated ECG data 260 may, for example, represent the raw ECG data 230 without or substantially without the artifacts.

In one embodiment, a clock 270 may be used by the processing system 220 to correlate, or otherwise compare and combine, the sensor data 210 from several different sensors on the patient in real time. The clock signal may also be shared with each of the sensors to provide a common timeframe. The data generated by each sensor may, in one embodiment, be automatically correlated (e.g., in time) or otherwise compared and combined. The combined or correlated data may be analyzed to identify significant noise components from one or more locations on the patient, including compression noise.

Such identified noise components may be used for a number of purposes. One purpose is to filter out the noise component and provide estimated real-time ECG data that may be used by the rescue worker without requiring the rescue worker to stop compressions in order to view usable ECG data. Another purpose may include notifying the rescuer that the ECG data is less reliable or unreliable because of the noise.

In one embodiment, an interdigitated electrode configuration can be used to measure raw ECG waveforms (including artifacts) and impedance variations causing artifacts substantially independently of each other. According to one embodiment, impedance measurements include measuring the change of impedance by applying plural superposed waveforms in a quadrature relationship to each other to the electrode, and computing the complex impedance from phase, amplitude, and frequency information detected. This information may be used in combination with other sensor information to identify artifacts in the ECG. In one example, the other sensor information may be data from one or more other sensors. According to a further embodiment, the artifacts may be removed in real-time using estimation techniques based on the real-time modeling of the compression-induced noise in the ECG signal.

FIG. 3 is a flow chart of a method 300 for processing raw ECG data and producing estimated real-time ECG data, according to another embodiment of the invention. At step 302, a physical non-cardiac influence on the raw ECG waveform data is sensed at a first location. At step 304, a time-domain computer model of the at least one physical, non-cardiac influence on the raw ECG waveform data is constructed. At step 306, the raw ECG waveform data is adaptively filtered, in the time domain, using the constructed time domain computer model of the physical, non-cardiac influence on the raw ECG waveform data to form the estimated real-time ECG waveform data.

According to another embodiment, in contrast to the adaptive non-continuous filters described above, a continuous filter may be used to filter out artifacts from the ECG data. The continuous filter may be synchronized to the chest compressions. In one example, one or more notch filters are used to filter out artifacts from ECG data. When multiple notch filters are used to remove the compression artifacts, the center frequency of the notch filter can correspond to the chest compression rate or two or more times that chest compression rate (e.g., harmonics of the chest compression rate). The chest compression rate may be determined using sensor data (including, but not limited to pressure sensors, impedance sensors, accelerometers, motion sensors, or other types of sensors), data provided by an automatic electro-mechanical chest compression device, or data derived from a calculation of compression rate based on the incoming raw ECG data. In one example, two filters are set to the compression frequency, two filters are set to the first harmonic of the compression frequency (where the first harmonic is equal to two times the compression frequency), and one filter is set to the second harmonic of the compression frequency (where the second harmonic is equal to three times the compression frequency). Optionally, additional filters may be used to filter out higher harmonics of the compression frequency. In another example, the center frequency of the notch filter corresponds to the most prominent frequency of the artifact.

Having thus described several aspects of at least one embodiment of the invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A method of processing electrocardiogram (ECG) waveform data of a patient into estimated real-time ECG waveform data, the method comprising:
   retrieving past ECG waveform data;
   segmenting the past ECG waveform data into a plurality of past ECG segments corresponding to a plurality of compression cycles of at least one physical non-cardiac influence;
   statistically processing the plurality of past ECG segments to generate representative segment of ECG artifact generated by a compression;
   sensing current ECG waveform data during a time interval that is subsequent to a sensing time of past ECG waveform data, the current ECG waveform data resembling an AC-coupled, low-pass filtered square wave characteristic of compression waveforms produced by an automatic electro-mechanical compression device;
   determining a fiducial point relating to a compression in the sensed current ECG waveform data;
   time aligning the current ECG waveform with the representative segment of ECG artifact based on the determined fiducial point for the compression in the sensed current ECG waveform data; and
   subtracting the representative segment of ECG artifact from the current ECG waveform to provide an estimation of a compression-free underlying ECG waveform.

2. The method of claim 1, wherein the ECG artifact is caused by repeated chest compressions.

3. The method of claim 1, further comprising detecting a frequency of repetition of the ECG artifact.

4. The method of claim 1, wherein sensing comprises measuring a change in impedance of an interface between an ECG electrode and the patient during chest compressions, and wherein statistically processing the plurality of past ECG segments to generate the representative segment of ECG artifact comprises determining an effect of the change in impedance on the past ECG waveform data.

5. The method of claim 4, wherein measuring the change in impedance comprises measuring a variation in complex impedances of the interface between the ECG electrode and the patient during the chest compressions over a range of frequencies lying between 30 kHz and 100 kHz.

6. The method of claim 4, wherein measuring the change in impedance comprises measuring a variation in complex impedances of the interface between the ECG electrode and the patient during the chest compressions over a range of frequencies lying between 30 kHz and 70 kHz.

7. The method of claim 4, wherein measuring the change in impedance comprises measuring a variation in complex impedances of the interface between the ECG electrode and the patient during the chest compressions at a frequency of about 35 kHz.

8. The method of claim 4, wherein measuring the change in impedance includes:

applying plural superposed waveforms in a quadrature relationship to each other to the electrode; and computing a complex impedance from detected phase, amplitude, and frequency information.

9. The method of claim 1, wherein sensing includes sensing the at least one physical non-cardiac influence on the ECG waveform at one of an ECG electrode, a pad placed beneath the patient, the patient's skin, an ECG monitoring device, a manually operated chest compression device, and an automatic electro-mechanical chest compression device.

10. The method of claim 1, wherein sensing includes detecting the at least one physical non-cardiac influence in the past ECG waveform data.

11. The method of claim 1, wherein sensing includes receiving data from a chest compression device including at least one of chest compression rate and chest compression force.

12. A medical device system, comprising:
an electrocardiogram (ECG) device for collecting ECG waveform data from a patient;
at least two ECG electrodes positioned on the patient and electrically coupled to the ECG device;
an automatic electro-mechanical chest compression device configured to apply chest compressions to the patient and to provide chest compression data to the processor in the form of an AC-coupled, low-pass filtered square waveform; and
a processor coupled to the ECG device and configured to:
retrieve past ECG waveform data;
segment the past ECG waveform data into a plurality of past ECG segments corresponding to a plurality of compression cycles of chest compressions,
statistically process the plurality of past ECG segments to generate a representative segment of ECG artifact generated by a compression,
generate a signal for the ECG device to collect current ECG waveform data during a time interval that is subsequent to a sensing time of past ECG waveform data,
determine a fiducial point relating to a compression in the sensed current ECG waveform data,
time align the current ECG waveform with the representative segment of ECG artifact based on the determined fiducial point for the compression in the sensed current ECG waveform data, and
subtract the representative segment of ECG artifact from the current ECG waveform to provide an estimation of a compression-free underlying ECG waveform.

13. The medical device system of claim 12, further comprising at least one first sensor for detecting the chest compressions applied to the patient.

14. The medical device system of claim 13, further comprising a second sensor, wherein the first sensor and the second sensor are configured to calculate impedance of an interface between at least one of the at least two ECG electrodes and the patient.

15. The medical device system of claim 13, wherein the at least one first sensor is located at one ECG electrode of the at least two ECG electrodes, a pad placed beneath the patient, the patient's skin, a manually operated chest compression device, and an automatic electro-mechanical chest compression device.

16. The medical device system of claim 12, wherein the processor is further configured to detect an artifact based on the past ECG waveform data.

17. The medical device system of claim 12, further comprising at least one continuous notch filter configured to filter the ECG waveform and provide a filtered ECG waveform to the processor, the at least one continuous notch filter including at least one first continuous notch filter having a center frequency corresponding to a frequency of the chest compressions.

18. The medical device system of claim 17, wherein the at least one continuous notch filter further includes at least one second continuous notch filter having the center frequency corresponding to a first harmonic of the frequency of the chest compressions.

* * * * *

UNITED STATES PATENT AND TRADEMARK OFFICE
CERTIFICATE OF CORRECTION

| | | |
|---|---|---|
| PATENT NO. | : 9,839,368 B2 | Page 1 of 1 |
| APPLICATION NO. | : 13/743891 | |
| DATED | : December 12, 2017 | |
| INVENTOR(S) | : Qing Tan, Frederick J. Geheb and Gary A. Freeman | |

It is certified that error appears in the above-identified patent and that said Letters Patent is hereby corrected as shown below:

On the Title Page

Column 2, Line 3, in the Abstract delete "sensing-at" and insert --sensing at--.

In the Claims

Claim 15
Column 12, Line 19, after "at one" insert --of an--.

Signed and Sealed this
Twenty-first Day of August, 2018

Andrei Iancu
*Director of the United States Patent and Trademark Office*